US011523993B1

(12) United States Patent
Shanmugam et al.

(10) Patent No.: US 11,523,993 B1
(45) Date of Patent: Dec. 13, 2022

(54) DOSAGE FORMS OF TAFAMIDIS AND ITS PHARMACEUTICALLY ACCEPTABLE SALT THEREOF

(71) Applicant: Nuray Chemicals Private Limited, Tamilnadu (IN)

(72) Inventors: Muthusamy Shanmugam, East Windsor, NJ (US); Ramasamy Venkatragavan, Tamil Nadu (IN); Singavarapu Ajay Madhukar, Tamil Nadu (IN); Erugu Balaiah, Tamil Nadu (IN); Palanisamy Sivakumar, Chennai (IN); Thirunavukkarasu Sakthikumar, Chennai (IN)

(73) Assignee: Nuray Chemicals Private Limited, Tamilnadu (IN)

( * ) Notice: Subject to any disclaimer, the term of this patent is extended or adjusted under 35 U.S.C. 154(b) by 0 days.

(21) Appl. No.: 17/530,003

(22) Filed: Nov. 18, 2021

(51) Int. Cl.
*A61K 9/48* (2006.01)
*A61K 9/20* (2006.01)
*A61K 31/167* (2006.01)

(52) U.S. Cl.
CPC .......... *A61K 9/4825* (2013.01); *A61K 9/2063* (2013.01); *A61K 31/167* (2013.01)

(58) Field of Classification Search
None
See application file for complete search history.

(56) References Cited

U.S. PATENT DOCUMENTS

| 2014/0377185 | A9 | 12/2014 | Mosher | |
|---|---|---|---|---|
| 2019/0092737 | A1* | 3/2019 | Brito | A61P 25/28 |
| 2021/0363116 | A1 | 11/2021 | Chen et al. | |

FOREIGN PATENT DOCUMENTS

| WO | 2020/128816 A2 | 6/2020 |
|---|---|---|
| WO | 2020/232325 A1 | 11/2020 |
| WO | 2021/001858 A1 | 1/2021 |
| WO | 2021/019448 A1 | 2/2021 |
| WO | 2021/093809 A1 | 5/2021 |

OTHER PUBLICATIONS

Vyndaqel® European Public assessment report, European Medicines Agency, Committee for Medicinal Products for Human Use (CHMP): 1-85 (2011).
Vyndaqel Full Prescribing Information, Pfizer Labs (2021).
Dissolution Conditions for Tafamidis and Tafamidis Meglumine, available online at www.accessdata.fda.gov/scripts/cder/dissolution/dsp_getalldata.cfm, last accessed on Nov. 12, 2021.
Remington: The Science and Practice of Pharmacy (1985), 19th Edition; 9 pages.
M. Ashford (Chapter 17) Pharmaceutics: The Science of Dosage Form Design, M.E. Aulton (Ed) (2006), pp. 234-252.
Regulatory Classification of Pharmaceutical Co-Crystals Guidance for Industry; (Feb. 2018); 7 pages.

* cited by examiner

*Primary Examiner* — David J Blanchard
*Assistant Examiner* — Sarah J Chickos
(74) *Attorney, Agent, or Firm* — Merchant & Gould P.C.; Daniel R. Evans (57) ABSTRACT

The disclosure relates to a novel dosage form comprising hard gelatin capsule having granule composition, spray dried or evaporated composition containing tafamidis or its pharmaceutically acceptable salt particularly tafamidis meglumine and tablet comprising tafamidis or its pharmaceutically acceptable salt particularly tafamidis meglumine that would not form a rigid gel upon contacting with water or buffer solution in dissolution specifically pH 6.8 phosphate buffer and that composition is indicated for the treatment of the cardiomyopathy of wild type or hereditary transthyretin-mediated amyloidosis in adults to reduce cardiovascular mortality and cardiovascular-related hospitalization.

29 Claims, 5 Drawing Sheets

DOSAGE FORMS OF TAFAMIDIS AND ITS PHARMACEUTICALLY ACCEPTABLE SALT THEREOF

FIELD OF THE INVENTION

The disclosure relates to a dosage form comprising tafamidis or a pharmaceutically acceptable salt thereof in the form of a hard gelatin capsule or tablet comprising a granule composition, a spray dried composition, evaporated composition, granules composition comprises acidifying agent or a combination thereof comprising tafamidis or a pharmaceutically acceptable salt thereof (e.g., tafamidis meglumine) that would not form a rigid gel upon contacting with water or buffer solution in dissolution specifically pH 6.8 phosphate buffer, wherein said compositions are indicated for the treatment of the cardiomyopathy of wild type or hereditary transthyretin-mediated amyloidosis in adults to reduce cardiovascular mortality and cardiovascular-related hospitalization.

BACKGROUND

Tafamidis is a selective stabilizer of transthyretin. Tafamidis is chemically known as 2-(3,5-dichlorophenyl)-1,3-benzoxazole-6-carboxylic acid with a molecular weight of 308.12 g/mol. Tafamidis meglumine is chemically known as 2-(3, 5-dichlorophenyl)-1,3-benzoxazole-6-carboxylic acid mono (1-deoxy-l-methylamino-D-glucitol) with a molecular weight of 503.33 g/mol.

Tafamidis and tafamidis meglumine are available as soft gelatin capsule form in United States, Europe and other markets. Tafamidis is marketed as Vyndamax®, while tafamidis meglumine is marketed as Vyndaqel®. The Vyndaqel® European Public assessment report states that "[d]uring development it was shown that tafamidis active substance, when formulated in a hard gelatin capsule with standard excipients, formed a rigid gel structure upon contact with aqueous vehicles thereby affecting the dissolution rate from the solid dosage." The Vyndaqel® European Public assessment report also states that "[b]ased on the initial dissolution results, it was decided to further enhance drug dispersibility and the dissolution rate using a soft gelatin capsule dosage form," and that "[b]ased on this the strategy was to prepare a water-dispersible drug suspension that would not form a gel upon contacting with water and encapsulate the suspension in a soft gelatin capsule." The Vyndaqel® European Public assessment report further states that "[a]suspension formulation was required as tafamidis showed poor solubility in many of the vehicles commonly used in formulating soft gelatin capsules and thus eliminated the option of developing the drug in a solution form," and that "selection and optimization of individual components of the proposed commercial formulation were discussed in detail."

According to the Vyndaqel® European Public assessment report "[t]he chosen excipients in the capsule fill solution are: polyethylene glycol (suspending vehicle), sorbitan monooleate (surfactant/wetting agent), polysorbate 80 (surfactant/wetting agent)," while "[t]he excipients in the capsule shell are: gelatin, propylene glycol, purified water, 'Sorbitol special-glycerin blend' (d-sorbitol, 1,4 sorbitan, mannitol and glycerin) and titanium dioxide (E 171) and black printing ink."

WO2021001858A1, WO2021019448A1, and WO2020232325A1, describe processes for the preparation of various polymorphic forms of tafamidis and tafamidis meglumine including an amorphous premix of tafamidis meglumine and spray drying of tafamidis meglumine to obtain amorphous tafamidis meglumine. These patent documents generally describe pharmaceutical compositions for tafamidis and its pharmaceutically acceptable salt, but are silent about manufacturing of particular composition.

WO2020128816A2 describes different conventional formulations of tafamidis and tafamidis meglumine without any information related to the stability challenges associated with a tafamidis-containing formulation.

During extensive investigations, it was discovered that tafamidis-containing dosage forms (e.g., hard-shell capsules and tablets) having acceptable drug dispersibility and dissolution rates may be obtained without using "special" ingredients. The inventors surprisingly found that the formation of rigid gels may be circumvented based on the formulated compositions disclosed herein.

OBJECT

The main objective of the disclosure relates to a pharmaceutically acceptable composition, preferably hard gelatin capsules, comprising tafamidis or tafamidis meglumine and one or more excipients, wherein formulated in a hard gelatin capsule with standard excipients, having easily water-dispersible carrier that would not form a rigid gel upon contacting water or buffer solution in dissolution a specifically in an official media of pH 6.8 phosphate buffer.

Another objective of the present disclosure relates to pharmaceutically acceptable tablet composition comprising standard excipients, having easily water-dispersible carrier that would not form a rigid gel upon contacting water or buffer solution in dissolution a specifically in an official media of pH 6.8 phosphate buffer.

SUMMARY

In present disclosure provides a hard gelatin capsule composition having easily dispersible granules for oral administration comprising:
 a) Tafamidis or its pharmaceutically acceptable salt;
 b) at least one acidifier; and
 c) at least one pharmaceutically acceptable excipient selected from the group consisting of at least one surfactant; disintegrant, binder, diluent, glidant and lubricant
 Or
A hard gelatin capsule composition having spray-dried or evaporated composition for oral administration comprising:
 a) Tafamidis or its pharmaceutically acceptable salt;
 b) at least one solubility enhancer;
 c) at least one disintegrant; and
 d) at least one pharmaceutically acceptable excipient.
In another aspect of the present disclosure is related to novel oral tablet composition comprising;
 a) Tafamidis or its pharmaceutically acceptable salt;
 b) at least one acidifier; and
 c) at least one pharmaceutically acceptable excipient selected from the group consisting of at least one surfactant; disintegrant, binder, diluent, glidant and lubricant.

DETAILED DESCRIPTION OF THE DRAWINGS

DETAILED DESCRIPTION

The information that follows illustrates various embodiments of the compositions disclosed herein. For the avoidance of doubt, it is specifically intended that any particular feature(s) described individually in any one of these paragraphs (or part thereof) may be combined with one or more other features described in one or more of the remaining paragraphs (or part thereof). In other words, it is explicitly intended that the features described below individually in each paragraph (or part thereof) represent important aspects of the invention that may be taken in isolation and also combined with other important aspects of the invention described elsewhere within this specification as a whole, and including the examples and figures. The skilled person will appreciate that the compositions claimed herein extends to such combinations of features and that these have not been recited in detail here in the interests of brevity.

Definitions of some of the terms used herein are detailed below.

The use of the terms "a" and "an" and "the" and similar references in the context of describing the liquid composition described herein (especially in the context of the following claims) are to be construed to cover both the singular and the plural, unless otherwise indicated herein or clearly contradicted by context.

The term "about" as used herein embodies standard error associated with a physico-chemical observable. As used herein, the term "about" means a slight variation of the value specified, for example, within 10% of the value specified. A stated amount for a compositional ingredient that is not preceded by the term "about" does not mean that there is no variance for the stated term, as one of ordinary skill would understand that there may be the possibility of a degree of variability generally associated with experimental error.

The term "therapeutically effective amount" or effective dose" as used herein refers to the amount or dose of tafamidis or tafamidis meglumine that is sufficient to initiate therapeutic response in a patient.

A first embodiment relates to hard gelatin capsule composition oral administration comprising: easily dispersible granules comprising a) tafamidis or a pharmaceutically acceptable salt thereof; b) at least one acidifier; and c) at least one pharmaceutically acceptable excipient selected from the group consisting of at least one surfactant; disintegrant, binder, diluent, glidant and lubricant.

A second embodiment relates to a hard gelatin capsule composition oral administration comprising spray-dried or evaporated composition comprising a) tafamidis or its pharmaceutically acceptable salt; b) at least one solubility enhancer; c) at least one disintegrant; and d) at least one pharmaceutically acceptable excipient.

In one aspect of the first or second embodiment, the hard gelatin capsule composition for oral administration comprises 20 mg of tafamidis meglumine.

In another aspect of the first or second embodiment, the hard gelatin capsule composition for oral administration comprises 61 mg of tafamidis.

In one aspect of the first embodiment, the granules comprise tafamidis or a pharmaceutically acceptable salt thereof, such as, for examples, tafamidis meglumine.

In another aspect of the first embodiment, the granules comprise tafamidis meglumine in an amount of about 20 mg per capsule.

In another aspect of the first embodiment, the granules comprises tafamidis in an amount of about 61 mg per capsule.

In another aspect of the second embodiment, the spray dried/evaporated solid composition comprises tafamidis or a pharmaceutically acceptable salt thereof.

In another aspect of the second embodiment, the spray dried/evaporated solid composition comprises tafamidis meglumine in an amount of about 20 mg per capsule.

In another aspect of the second embodiment, the spray dried/evaporated solid composition comprises tafamidis in an amount of about 61 mg per capsule.

A third embodiment relates to a table composition comprising tafamidis or a pharmaceutically acceptable salt; b) at least one acidifier; and c) at least one pharmaceutically acceptable excipient selected from the group consisting of at least one surfactant; disintegrant, binder, diluent, glidant and lubricant.

In one aspect of the third embodiment, the tablet comprises tafamidis meglumine in an amount of about 20 mg per tablet.

In another aspect of the third embodiment, the tablet comprises tafamidis in an amount of about 61 mg per tablet.

In one aspect of an embodiment disclosed herein, the composition may comprise at least one acidifier which may be a pharmaceutically acceptable organic acid, inorganic acid, or a combination thereof. Examples of pharmaceutically acceptable organic acids and inorganic acids include, but are not limited to hydrochloric acid, hydrobromic acid, hydroiodic acid, sulfuric acid, sulfamic acid, phosphoric acid, nitric acid, citric acid, tartaric acid, malic acid, fumaric acid, salicylic acid, p-toluenesulfonic acid, methanesulfonic acid, oxalic acid, succinic acid, lactic acid, or a combination thereof. As explained in greater detail herein, an unexpected discovery regarding the development work disclosed herein is that an acidifier inhibits gel formation during the dissolution. In one aspect, the acidifier comprises hydrochloric acid, phosphoric acid, citric acid, tartaric acid, malic acid, fumaric acid, succinic acid, lactic acid, or a combination thereof.

In one aspect of an embodiment disclosed herein, the at least one acidifier may be present in an amount of from about 0.1% w/w to about 10% w/w based on the total weight of the composition, including all values in between, such as, for example, about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, about 6.5% w/w, about 7.0% w/w, about 7.5% w/w, about 8.5% w/w, about 9.0% w/w, and about 9.5% w/w.

In yet another aspect of an embodiment disclosed herein, the composition may comprise at least one surfactant. Examples of surfactants include but are not limited to sodium lauryl sulfate, poloxamer, glyceryl monostearate, glyceryl monolaurate, sorbitan monolaurate, sorbitan monostearate, polyethylene glycols, or a combination thereof. Observations made during development work shows that the at least one surfactant may increase in vivo bioavailability upon oral administration of a composition disclosed herein.

In one aspect of an embodiment disclosed herein, the at least one surfactant may be present in an amount of from about 0.1% w/w to about 10% w/w based on the total weight of the composition, including all values in between, such as, for example, about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, about 6.5% w/w, about 7.0% w/w, about 7.5% w/w, about 8.5% w/w, about 9.0% w/w, and about 9.5% w/w.

In one aspect of an embodiment disclosed herein, the composition may comprise at least one disintegrant. Examples of disintegrants include, but are not limited to, crospovidone, croscarmellose sodium, low hydroxypropyl cellulose, starch, sodium starch glycolate, microcrystalline cellulose, alginic acid, polacrillin potassium, or a combination thereof.

In one aspect of an embodiment disclosed herein, the at least one disintegrant may be present in an amount of from about 0% w/w to about 10% w/w based on the total weight of the composition, including all values in between, such as, for example, about 0.05% w/w, about 0.1% w/w, about 0.2% w/w, about 0.3% w/w, about 0.4% w/w, about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, about 6.5% w/w, about 7.0% w/w, about 7.5% w/w, about 8.5% w/w, about 9.0% w/w, and about 9.5% w/w.

In one aspect of an embodiment disclosed herein, the composition may comprise at least one binder. Examples of binders include but are not limited to povidone, starch, gelatin, hydroxypropyl cellulose, hydroxypropyl methylcellulose, methyl cellulose, carboxymethyl cellulose, or a combination thereof In one aspect of an embodiment disclosed herein, the at least one binder may be present in an amount of from about 0% w/w to about 10% w/w based on the total weight of the composition, including all values in between, such as, for example, about 0.05% w/w, about 0.1% w/w, about 0.2% w/w, about 0.3% w/w, about 0.4% w/w, about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, about 6.5% w/w, about 7.0% w/w, about 7.5% w/w, about 8.5% w/w, about 9.0% w/w, and about 9.5% w/w.

In one aspect of an embodiment disclosed herein, the composition may comprise at least one diluent. Examples of diluents include, but are not limited to lactose, microcrystalline cellulose, starch, dicalcium phosphate, mannitol, xylitol, sorbitol, dextrose, fructose, sucrose, maltodextrin, or a combination thereof.

In one aspect of an embodiment disclosed herein, the at least one diluent may be present in an amount of from about 0% w/w to about 90% w/w based on the total weight of the composition, including all values in between, such as, for example, about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, about 6.5% w/w, about 7.0% w/w, about 7.5% w/w, about 8.5% w/w, about 9.0% w/w, about 9.5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, and about 85% w/w.

In one aspect of an embodiment disclosed herein, the composition may comprise at least one solubility enhancer. Examples of solubility enhancers include, but are not limited to, α-cyclodextrin, γ-cyclodextrin, β-cyclodextrin (and derivatives thereof; see, e.g., U.S. Patent Application Publication No. 2014/0377185 A9), hydroxypropyl-β-cyclodextrin, povidone, copovidone, polyethylene glycol, sorbitol monooleate polysorbate, or a combination thereof.

In one aspect of an embodiment disclosed herein, the at least one solubility enhancer may be present in an amount of from about 0% w/w to about 90% w/w based on the total weight of the composition, including all values in between, such as, for example, about 0.5% w/w, about 1.0% w/w, about 1.5% w/w, about 2.0% w/w, about 2.5% w/w, about 3.0% w/w, about 3.5% w/w, about 4.0% w/w, about 4.5% w/w, about 5.0% w/w, about 5.5% w/w, about 6.5% w/w, about 7.0% w/w, about 7.5% w/w, about 8.5% w/w, about 9.0% w/w, about 9.5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, and about 85% w/w.

In one aspect of an embodiment disclosed herein, the composition may comprise at least one glidant. Examples of glidants include, but are not limited to, colloidal silicon dioxide, magnesium trisilicate, starch, talc, or a combination thereof In one aspect of an embodiment disclosed herein, the at least one glidant may be present in an amount of from about 0% w/w to about 2% w/w based on the total weight of the composition, including all values in between, such as, for example, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, and about 1.9% w/w.

In one aspect of an embodiment disclosed herein, the composition may comprise at least one lubricant. Examples of lubricants include, but are not limited to, calcium stearate, glycerin monostearate, glyceryl behenate, glyceryl palmitostearate, hydrogenated castor oil, hydrogenated vegetable oil type I, light mineral oil, magnesium lauryl sulfate, magnesium stearate, medium-chain triglycerides, mineral oil, myristic acid, palmitic acid, poloxamer, polyethylene glycol, sodium stearyl fumarate, stearic acid, talc, zinc stearate, or a combination thereof.

In one aspect of an embodiment disclosed herein, the at least one lubricant may be present in an amount of from about 0% w/w to about 2% w/w based on the total weight of the composition, including all values in between, such as, for example, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, and about 1.9% w/w.

In one aspect of an embodiment disclosed herein, the capsule composition or the tablet composition does not form a gel during dissolution in a suitable medium.

Capsule compositions disclosed herein comprise a hard capsule having a capsule size suitable based on the total amount of the capsule composition. Examples of suitable capsule sizes include, for example, #0, #1, #2, #3, and #4.

EXAMPLES

The following exemplified embodiments illustrate aspects of the solid composition disclosed herein and should not be considered to be limiting on the subject matter claimed herein.

The FDA recommends two dissolution methods for tafamidis and tafamidis meglumine.

The dissolution method for tafamidis (capsule) utilizes a USP II (Paddle) apparatus with sinker operating at a speed of 75 rpm and a medium volume of 900 mL, where the Tier I Medium comprises 0.05 M (50 mM) Sodium Phosphate Buffer, pH 6.8 with 1.0% Tween 80 and the Tier II Medium comprises 0.05 M (50 mM) Sodium Phosphate Buffer, pH 6.8 with 1.0% Tween 80 and enzyme with protease activity as per USP. The recommended sampling times are 5, 10, 15, 20, 30, and 45 minutes.

The dissolution method for tafamidis meglumine (capsule) utilizes a USP II (Paddle) apparatus with sinker operating at a speed of 75 rpm and a medium volume of 900 mL, where the Tier 1 Medium comprises 0.05 M (50 mM) Sodium Phosphate Buffer, pH 6.8, and the Tier 2 Medium comprises 0.05 M (50 mM) Sodium Phosphate Buffer, pH 6.8, and pancreatin with protease activity as per USP. The recommended sampling times are 5, 10, 15, 20, 30, and 45 minutes.

The FDA recommended dissolution medium disclosed herein may be referred to as the "official media" or "official medium (OGD)."

Example 1. Tafamidis Meglumine Capsules

Table 1 provides the compositional makeup of a capsule composition (Ex. 1) comprising tafamidis meglumine and at least one pharmaceutically acceptable excipient.

TABLE 1

| Compositional makeup of Example 1 | |
|---|---|
| Ingredients(s) | mg/capsule |
| Tafamidis meglumine | 20.00 |
| Lactose monohydrate | 108.00 |
| Maize starch | 5.00 |
| Croscarmellose sodium | 5.00 |
| Syloid 244 FP | 3.00 |
| Sodium lauryl sulfate | 1.00 |
| Magnesium stearate | 1.00 |
| Capsule fill weight | 200.00 |

Manufacturing Process

Accurately weighed tafamidis meglumine, sodium lauryl sulfate and syloid 244 FP (e.g., silica glident) were sifted using #30. Weighed lactose monohydrate, maize starch, croscarmellose sodium, were sifted using #20. Both #30 mesh and #20 mesh materials were blended for 15 min. The above blend was lubricated using #40 mesh sifted magnesium stearate for 5 min. The lubricated blend was filled into hard gelatin capsules with average fill weight of 200.00 mg. The dissolution testing was performed for capsules using USP II (paddle) apparatus, 900 mL of pH 6.8 phosphate buffer at 75 rpm.

Example 2. Tafamidis Meglumine Capsules

Table 2 provides the compositional makeup of a capsule composition (Ex. 2) comprising tafamidis meglumine and at least one pharmaceutically acceptable excipient.

TABLE 2

| Compositional makeup of Example 2 | |
|---|---|
| Ingredients(s) | mg/capsule |
| Tafamidis meglumine | 20.00 |
| Povidone K30 | 10.00 |
| Sodium lauryl sulfate | 4.00 |
| Polysorbate 80 | 2.50 |
| Purified water | qs |
| Lactose monohydrate | 369.50 |
| Crospovidone | 15.00 |
| Colloidal silicon dioxide | 4.00 |
| Capsule fill weight | 450.00 |

Manufacturing Process

Accurately weighed tafamidis meglumine, sodium lauryl sulfate, polysorbate 80, povidone K30 were added into purified water and mixed well. Weighed lactose monohydrate and crospovidone were sifted using #20. Mesh #20 sifted materials were granulated (top spray granulation) using tafamidis meglumine dispersion. The above blend was mixed with #40 mesh sifted colloidal silicon dioxide for 5 min. The blend was filled into hard gelatin capsules with average fill weight of 450.00 mg. The dissolution testing was performed for capsules using USP II (paddle) apparatus, 900 mL of pH 6.8 phosphate buffer at 75 rpm.

Example 3. Tafamadis Meglumine Capsules

Table 3 provides the compositional makeup of a capsule composition (Ex. 3) comprising tafamidis meglumine and at least one pharmaceutically acceptable excipient.

TABLE 3

| Compositional makeup of Example 3 | |
|---|---|
| Ingredients(s) | Example 3 mg/capsule |
| Tafamidis meglumine | 20.00 |
| Povidone K30 | 20.00 |
| Polacrillin potassium | 10.00 |
| Mannitol SD 200 | 147.40 |
| Colloidal silicon dioxide | 2.00 |
| Magnesium Stearate | 0.60 |
| Capsule fill weight | 200.00 |

Manufacturing Process

Accurately weighed tafamidis meglumine, polacrillin potassium, mannitol SD 200, povidone K30 were added into purified water and mixed for 30 min to form complex with povidone K30. The resulting dispersion were dried in tray dryer and milled. The above milled materials were mixed with #40 mesh sifted colloidal silicon dioxide and magnesium stearate for 5 min. The blend was filled into hard gelatin capsules with average fill weight of 200.00 mg. The dissolution testing was performed for capsules using USP II (paddle) apparatus, 900 mL of pH 6.8 phosphate buffer at 75 rpm.

Example 4. Tafamidis Meglumine Capsules

Table 4 provides the compositional makeup of a capsule composition (Ex. 4) comprising tafamidis meglumine and at least one pharmaceutically acceptable excipient.

TABLE 4

Compositional makeup of Example 4

| Ingredients(s) | Example 4 mg/capsule |
|---|---|
| Tafamidis meglumine | 20.00 |
| Poloxamer 188 | 20.00 |
| Croscarmellose sodium | 10.00 |
| Mannitol SD 200 | 147.40 |
| Colloidal silicon dioxide | 2.00 |
| Magnesium Stearate | 0.60 |
| Capsule fill weight | 200.00 |

Manufacturing Process

Accurately weighed tafamidis meglumine, poloxamer P188, croscarmellose sodium, mannitol SD 200 were added into purified water and mixed for 30 min. The resulting dispersion were dried in tray dryer and milled. The above milled materials were mixed with #40 mesh sifted colloidal silicon dioxide and magnesium stearate for 5 min. The blend was filled into hard gelatin capsules with average fill weight of 200.00 mg.

Table 5 presents dissolution test results for the compositions of Examples 1-2. The dissolution testing was performed for capsules using USP II (paddle) apparatus, 900 mL of pH 6.8 phosphate buffer at 75 rpm.

TABLE 5

Dissolution Data for Examples 1-2

Dissolution at 50 mM Sodium phosphate buffer pH 6.8, 900 mL, 75 rpm, USP II (Paddle) Q point at 30 min
% drug release

| Example(s) | 5 min | 10 min | 15 min | 20 min | 30 min | 45 min | 60 min | Observation |
|---|---|---|---|---|---|---|---|---|
| Example 1 | 2 | 3 | 6 | 5 | 8 | 9 | 12 | A rigid gel formed |
| Example 2 | — | 24 | 20 | 24 | 32 | 34 | 44 | |

Figure 1:
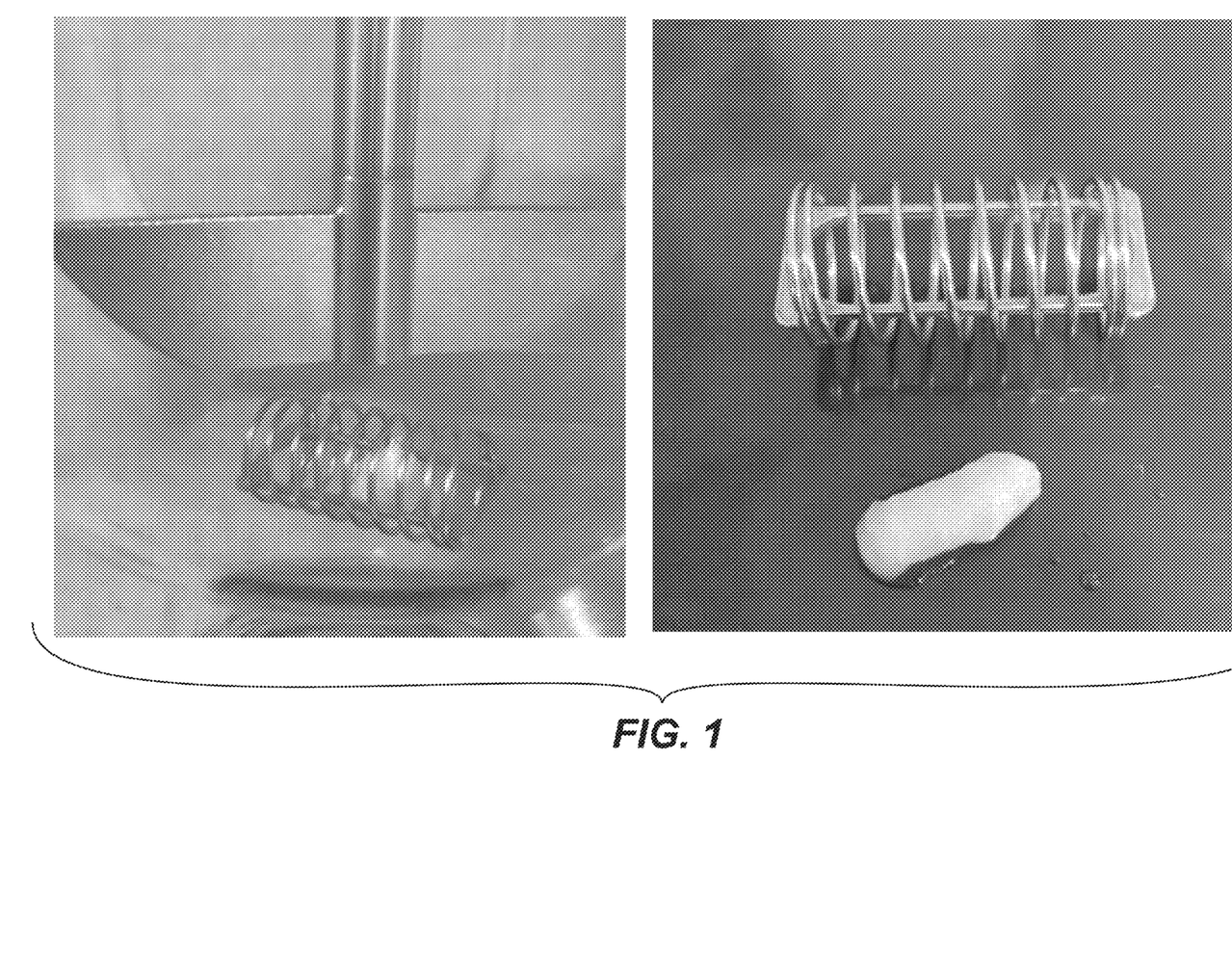
FIG. 1: Formation of a rigid gel in hard gelatin capsule prepared as per example-1 containing tafamidis meglumine granules in pH 6.8 Phosphate buffer at 30 minutes (Q point).
Figure 2:
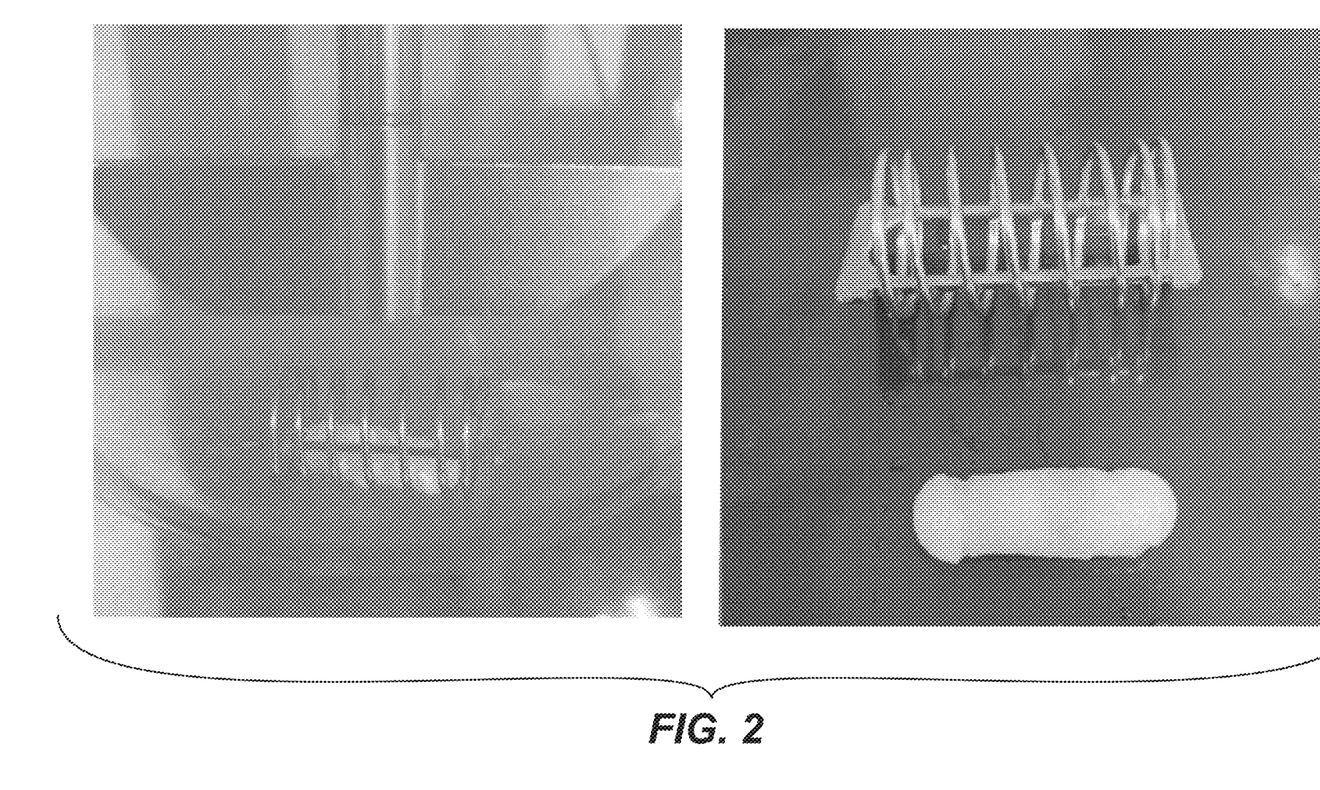
FIG. 2: Formation of a rigid gel in hard gelatin capsule prepared as per example-2 containing tafamidis meglumine granules in pH 6.8 Phosphate buffer at 30 minutes (Q point).
Figure 3:
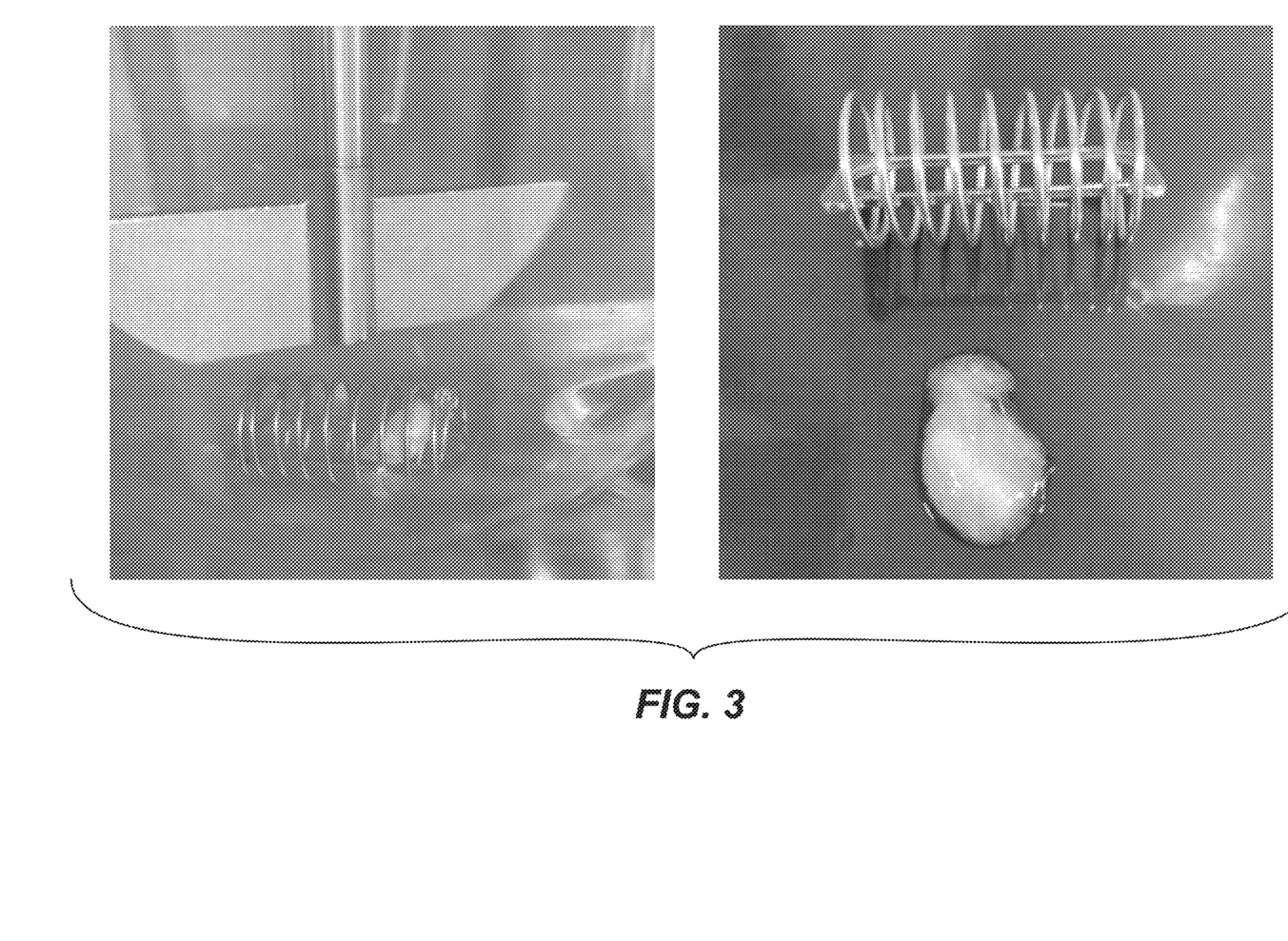
FIG. 3: Formation of gel in hard gelatin capsule prepared as per example-3 containing tafamidis meglumine granules in pH 6.8 Phosphate buffer at 30 minutes (Q point).
Figure 4:
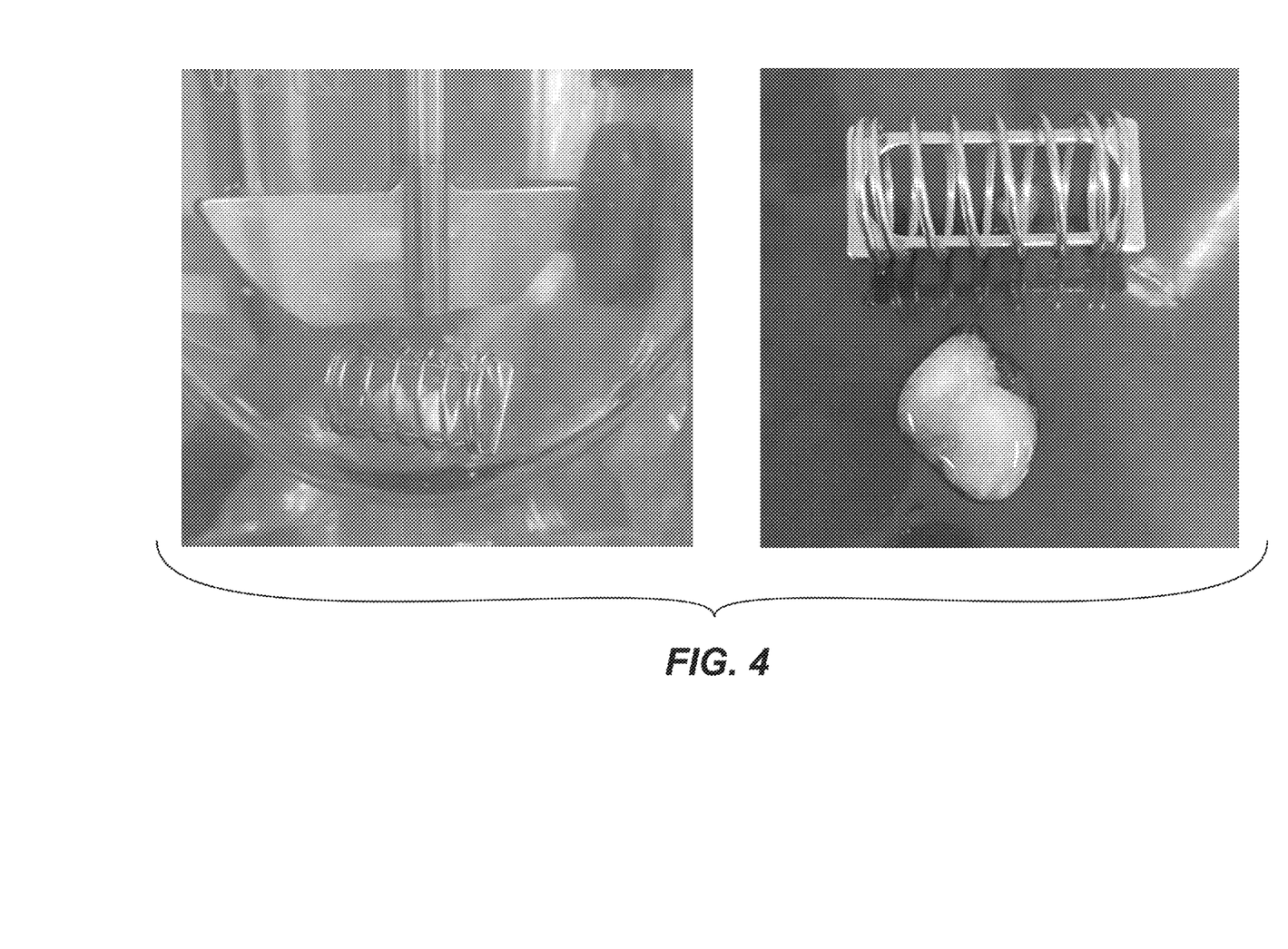
FIG. 4: Formation of gel in hard gelatin capsule prepared as per example-4 containing tafamidis Meglumine granules in pH 6.8 Phosphate buffer at 30 minutes (Q point).
Figure 5:
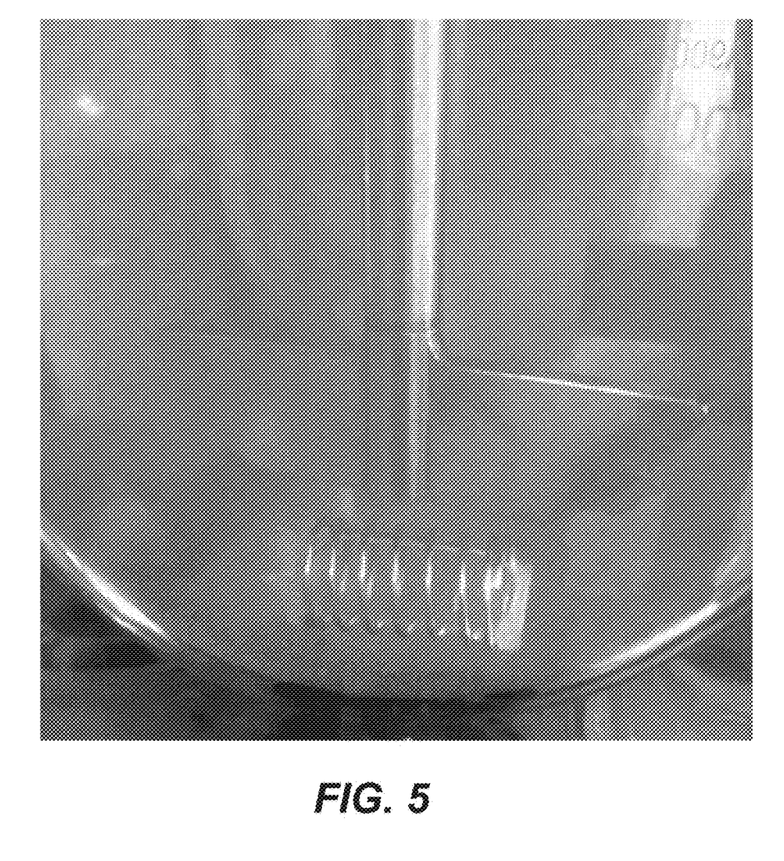
FIG. 5: No gel/gel structured mucilage formation in pH 6.8 Phosphate buffer at 30 minutes (Q point) of hard gelatin capsule prepared as per Example-6 containing tafamidis meglumine granules with organic acid i.e. citric acid anhydrous.

The Table 5 data shows that a rigid gel formed for the capsule compositions of Examples 1-2. FIGS. 1-4 depict the observed capsule gels formed for Examples 1-4, respectively. Hard gelatin capsule formulations containing granules with the identified excipients, formed a rigid gel structure upon contact with aqueous vehicles, i.e., pH 6.8 phosphate buffer thereby affecting the dissolution rate or drug release rate from the solid dosage.

Examples 5-7. Tafamidis Meglumine Capsules (Organic Acidifier Granules)

Table 6 provides the compositional makeup of capsule compositions (Exs. 5-7) comprising tafamidis meglumine and at least one pharmaceutically acceptable excipient.

TABLE 6

Compositional makeup of Examples 5-7 (granules)

| Ingredients(s) | Example 5 | Example 6 mg/capsule | Example 7 |
|---|---|---|---|
| Tafamidis meglumine | 20.00 | 20.00 | 20.00 |
| Mannitol SD 200 | 347.00 | — | — |
| Lactose monohydrate | — | 422.50 | — |
| Microcrystalline cellulose | — | — | 382.25 |
| Povidone K30 | — | 15.00 | 9.00 |
| Croscarmellose sodium | 20.00 | 25.00 | 22.50 |
| Sodium lauryl sulfate | 2.00 | 5.00 | 4.50 |
| Citric acid anhydrous | 5.00 | 5.00 | 5.00 |
| Silicon dioxide | 4.00 | 5.00 | 4.50 |
| Magnesium Stearate | 4.00 | 2.50 | 2.25 |
| Capsule fill weight | 402.00 | 500.00 | 450.00 |

Manufacturing Process for Example 5

Accurately weighed Tafamidis meglumine, mannitol SD 200, croscarmellose sodium, sodium lauryl sulfate was sifted using #30. Mesh #30 sifted materials were granulated in High shear mixer granulator using citric acid anhydrous solution. The wet mass was dried and milled, the dried blend was mixed with #40 mesh sifted colloidal silicon dioxide and magnesium stearate for 5 min. The blend was filled into hard gelatin capsules with average fill weight of 402.00 mg. The dissolution testing was performed for capsules using USP II (paddle) apparatus, 900 mL of pH 6.8 phosphate buffer at 75 rpm.

Manufacturing Process For Example 6:

Accurately weighed Tafamidis meglumine, lactose monohydrate, povidone K30, croscarmellose sodium, sodium lauryl sulfate was sifted using #30. Mesh #30 sifted materials were granulated in High shear mixer granulator using citric acid anhydrous solution. The wet mass was dried and milled, the dried blend was mixed with #40 mesh sifted colloidal silicon dioxide and magnesium stearate for 5 min. The blend was filled into hard gelatin capsules with average fill weight of 500.00 mg. The dissolution testing was performed for capsules using USP II (paddle) apparatus, 900 mL of pH 6.8 phosphate buffer at 75 rpm.

Manufacturing Process For Example 7:

Accurately weighed Tafamidis meglumine, microcrystalline cellulose, povidone K30, croscarmellose sodium, sodium lauryl sulfate was sifted using #30. Mesh #30 sifted materials were granulated in High shear mixer granulator using citric acid anhydrous solution. The wet mass was dried and milled, the dried blend was mixed with #40 mesh sifted colloidal silicon dioxide and magnesium stearate for 5 min. The blend was filled into hard gelatin capsules with average fill weight of 450.00 mg.

Table 7 presents dissolution test results for the compositions of Examples 5-7. The dissolution testing was performed for capsules using USP II (paddle) apparatus, 900 mL of pH 6.8 phosphate buffer at 75 rpm.

TABLE 7

Dissolution Data for Examples 5-7

Dissolution at 50 mM Sodium phosphate buffer pH 6.8, 900 mL, 75 rpm, USP II (Paddle), Q point at 30 min
% drug release

| Example(s) | 5 min | 10 min | 15 min | 20 min | 30 min | 45 min | 60 min | Observation |
|---|---|---|---|---|---|---|---|---|
| Example 5 | 64 | 79 | 84 | 88 | 90 | 93 | 94 | No gel |
| Example 6 | 65 | 84 | 90 | 92 | 95 | 96 | 97 | observed |
| Example 7 | 34 | 70 | 79 | 85 | 90 | 93 | 95 | formations were |

Based on the Table 7 data, it may be seen that, e.g., Example 6 shows the method of manufacturing a solid composition with an acidifier in granules filled into hard gelatin capsules overcomes the gel formation in dissolution preferably in tafamidis meglumine capsules 20 mg official media (OGD) of 50 mM Sodium phosphate buffer pH 6.8, 900 mL, 75 rpm, USP II (Paddle), Q point at 30 min.

Examples 5-7 demonstrate a solid pharmaceutical formulations having various composed granules with acidifiers filled into hard gelatin capsules makes the tafamidis meglumine granules to disperse easily or within 5 to 7 minutes without the formation of a gel or gel structured mucilage formation upon contact with water or any buffer solution preferably in tafamidis meglumine capsules 20 mg official media (OGD) of 50 mM Sodium phosphate buffer pH 6.8, 900 mL, 75 rpm, USP II (Paddle), Q point at 30 min.

Example 8. Tafamidis Meglumine Capsules (Organic Acidifier Granules)

Table 6 provides the compositional makeup of a capsule composition (Ex. 8) comprising tafamidis and at least one pharmaceutically acceptable excipient.

TABLE 8

Compositional makeup of Example 8

| Ingredients(s) | Example 8 mg/capsules |
|---|---|
| Tafamidis | 61.00 |
| Lactose monohydrate | 294.00 |
| Povidone K30 | 10.00 |
| Croscarmellose sodium | 20.00 |
| Sodium lauryl sulfate | 4.00 |
| Citric acid anhydrous | 5.00 |
| Silicon dioxide | 4.00 |
| Magnesium Stearate | 2.00 |
| Capsule fill weight | 400.00 |

Manufacturing Process

Accurately weighed tafamidis, lactose monohydrate, povidone K30, croscarmellose sodium, sodium lauryl sulfate was sifted using #30. Mesh #30 sifted materials were granulated in High shear mixer granulator using citric acid anhydrous solution. The wet mass was dried and milled, the dried blend was mixed with #40 mesh sifted colloidal silicon dioxide and magnesium stearate for 5 min. The blend was filled into hard gelatin capsules with average fill weight of 400.00 mg.

Table 9 presents dissolution test results for the composition of Example 8. The dissolution testing was performed for capsules using USP II (paddle) apparatus, 900 mL of pH 6.8 phosphate buffer at 75 rpm.

TABLE 9

Dissolution data for Example 8

Dissolution at 50 mM Sodium phosphate buffer pH 6.8 + 1% Tween 80, 900 mL, 75 rpm, USP II (Paddle), Q point at 30 min
% drug release

| Example | 5 min | 10 min | 15 min | 20 min | 30 min | 45 min | 60 min | Observation |
|---|---|---|---|---|---|---|---|---|
| Example 8 | 64 | 79 | 84 | 88 | 90 | 93 | 94 | No gel formations were observed |

Based on the Table 9 data, it may be seen that the Example 8 composition shows the method of manufacturing a solid composition with acidifying agent in granules filled into hard gelatin capsules overcomes the gel formation in dissolution preferably in tafamidis capsules 61 mg official media (OGD) of 50 mM Sodium phosphate buffer pH 6.8+1% Tween 80, 900 mL, 75 rpm, USP II (Paddle), Q point at 30 min.

Example 8 demonstrates a solid pharmaceutical formulations comprising granules with acidifiers filled into hard gelatin capsules makes the tafamidis granules to disperse easily (e.g., within 5 to 7 minutes) without the formation of a gel or gel structured mucilage formation upon contact with water or any buffer solution preferably in tafamidis capsules 61 mg official media (OGD) of 50 mM Sodium phosphate buffer pH 6.8+1% Tween 80, 900 mL, 75 rpm, USP II (Paddle), Q point at 30 min.

Example 9. Tafamidis Meglumine Capsules

Table 10 provides the compositional makeup of a capsule composition (Ex. 9) comprising tafamidis meglumine and at least one pharmaceutically acceptable excipient.

TABLE 10

Compositional makeup of Example 9

| Ingredients(s) | mg/capsule |
|---|---|
| Tafamidis meglumine | 20.00 |
| Lactose monohydrate | 108.00 |
| Maize starch | 5.00 |
| Croscarmellose sodium | 5.00 |
| Syloid 244 FP | 3.00 |
| Sodium lauryl sulfate | 1.00 |
| Magnesium stearate | 1.00 |
| Capsule fill weight | 200.00 |

Example 10. Tafamidis Meglumine Capsules

Table 11 provides the compositional makeup of a capsule composition (Ex. 10) comprising tafamidis meglumine and at least one pharmaceutically acceptable excipient.

TABLE 11

Compositional makeup of Example 10

| Ingredients(s) | mg/capsule |
|---|---|
| Tafamidis meglumine | 20.00 |
| Hydroxypropyl β-cyclodextrin | 20.00 |
| Sodium lauryl sulfate | 0.20 |

TABLE 11-continued

Compositional makeup of Example 10

| Ingredients(s) | mg/capsule |
|---|---|
| Purified water | qs |
| Lactose monohydrate | 74.04 |
| Crospovidone | 4.80 |
| Colloidal silicon dioxide | 0.96 |
| Capsule fill weight | 120.00 |

Table 12 presents dissolution test results for the compositions of Examples 9-10.

TABLE 12

Dissolution Data for Examples 9-10

Dissolution at 50 mM Sodium phosphate buffer pH 6.8, 900 mL, 75 rpm, USP II (Paddle)
% drug release

| Example(s) | 5 min | 10 min | 15 min | 20 min | 30 min | 45 min | 60 min | Observation |
|---|---|---|---|---|---|---|---|---|
| Example 9 | 2 | 3 | 6 | 5 | 8 | 9 | 12 | Rigid gel formed |
| Example 10 | — | 24 | 20 | 24 | 32 | 34 | 44 | |

Examples 11-12. Tafamidis Meglumine Capsules (Spray-Dried)

Table 13 provides the compositional makeup of a capsule compositions (Exs. 11-12) comprising tafamidis meglumine and at least one pharmaceutically acceptable excipient.

TABLE 13

Compositional makeup of Examples 11-12 (spray-dried)

| Ingredients(s) | Example 11 mg/capsule | Example 12 mg/capsule |
|---|---|---|
| Tafamidis meglumine | 20.00 | 20.00 |
| Hydroxypropyl β-cyclodextrin | 20.00 | 100.00 |
| Purified water | qs | qs |
| Capsule fill weight | 40.00 | 120.00 |

Table 14 presents dissolution test results for the compositions of Examples 11-12.

TABLE 14

Dissolution data for Examples 11-12

Dissolution at 50 mM Sodium phosphate buffer pH 6.8, 900 mL, 75 rpm, USP II (Paddle)
% drug release

| Example(s) | 5 min | 10 min | 15 min | 20 min | 30 min | 45 min | 60 min | Observation |
|---|---|---|---|---|---|---|---|---|
| Example 11 | 5 | 11 | 16 | 18 | 23 | 26 | 29 | Rigid gel formed |
| Example 12 | — | 94 | 97 | 98 | 97 | 97 | 97 | No gel formation observed |

Examples 13-14. Tafamidis Meglumine Capsules (Spray-Dried)

Table 11 provides the compositional makeup of a capsule compositions (Exs. 13-14) comprising tafamidis meglumine and at least one pharmaceutically acceptable excipient.

TABLE 15

Compositional makeup of Examples 13-14 (spray-dried)

| Ingredients(s) | Example 13 mg/capsule | Example 14 mg/capsule |
|---|---|---|
| Tafamidis meglumine | 20.00 | 20.00 |
| β-cyclodextrin | 100.00 | 100.00 |
| Lactose monohydrate | 68.00 | 68.00 |
| Crospovidone | 10.00 | 10.00 |
| Purified water | qs | qs |
| Capsule fill weight | 198.00 | 198.00 |
| | Tafamidis meglumine+ β-cyclodextrin dissolved in required quantity of water | Tafamidis meglumine+ β-cyclodextrin dispersed in less quantity of water |

Table 16 presents dissolution test results for the compositions of Examples 13-14.

TABLE 16

Dissolution data for Examples 13-14

Dissolution at 50 mM Sodium phosphate buffer pH 6.8, 900 mL, 75 rpm, USP II (Paddle)
% drug release

| Example(s) | 5 min | 10 min | 15 min | 20 min | 30 min | 45 min | 60 min | Observation |
|---|---|---|---|---|---|---|---|---|
| Example 13 | 41 | 80 | 93 | 95 | 96 | 96 | 95 | No gel observed formation |
| Example 14 | 65 | 92 | 94 | 94 | 94 | 95 | 95 | |

Example 15. Tafamidis Capsules (Spray-Dried)

Table 17 provides the compositional makeup of a capsule composition (Ex. 15) comprising tafamidis and at least one pharmaceutically acceptable excipient.

TABLE 17

Compositional makeup of Example 15 (spray-dried)

| Ingredients(s) | Example 15 mg/capsule |
|---|---|
| Tafamidis | 61.00 |
| β-cyclodextrin | 305.00 |
| Lactose monohydrate | 61.50 |
| Crospovidone | 22.50 |
| Purified water | qs |
| Capsule fill weight | 450.00 |
| | Tafamidis + β-cyclodextrin dispersed in required quantity of water |

Table 18 presents dissolution test results for the composition of Example 15.

TABLE 18

Dissolution Data for Example 15

Dissolution at 50 mM Sodium phosphate buffer
pH 6.8, 900 mL, 75 rpm, USP II (Paddle)
% drug release

| Example(s) | 5 min | 10 min | 15 min | 20 min | 30 min | 45 min | 60 min | Observation |
|---|---|---|---|---|---|---|---|---|
| Example 15 | 38 | 82 | 97 | 98 | 98 | 98 | 99 | No gel formation observed |

Table 19 provides a qualitative composition of tafamidis Tablets (61 mg) and tafamidis meglumine Tablets (20 mg).

TABLE 19

Qualitative Tablet Compositions

| Tafamidis Tablets 61 mg | Tafamidis meglumine Tablets 20 mg | Function category |
|---|---|---|
| Tafamidis | Tafamidis meglumine | API |
| Lactose monohydrate | Lactose monohydrate | Diluent |
| Microcrystalline cellulose | Microcrystalline cellulose | Diluent |
| Croscarmellose sodium | Croscarmellose sodium | Disintegrant |
| Sodium Lauryl Sulfate | Sodium Lauryl Sulfate | Surfactant |
| Citric acid anhydrous | Citric acid anhydrous | Acidifier |
| Povidone | Povidone | Binder |
| Colloidal silicon dioxide | Colloidal silicon dioxide | Glidant |
| Magnesium stearate | Magnesium stearate | Lubricant |

Example 16. Tafamidis Meglumine Tablets (With Lactose Monohydrate And Microcrystalline Cellulose)

Tafamidis meglumine Tablets 20 mg prototype composition with lactose monohydrate 200 mesh and microcrystalline cellulose (Vivapur PH 101) with povidone (Povidone K30) as binder by wet granulation process. Table 20 provides the compositional makeup of the Example 15 tablet composition.

TABLE 20

Compositional makeup of Example 16

| Ingredients | Example 16 mg/tablet |
|---|---|
| Intra-granular portion | |
| Tafamidis meglumine | 20.00 |
| Lactose monohydrate 200 mesh | 65.30 |
| Microcrystalline cellulose (Vivapur pH 101) | 40.00 |
| Croscarmellose sodium (Vivasol) | 3.50 |
| Sodium lauryl sulfate (Stepanol WA-100) | 1.40 |
| Granulating fluid | |
| Purified water | qs |
| Povidone (Kollidon K30) | 3.50 |
| Extra-granular portion | |
| Croscarmellose sodium (Vivasol) | 3.50 |
| Colloidal silicon dioxide (Aerosil 200) | 1.40 |
| Magnesium stearate | 1.40 |
| Total Tablet weight | 140.00 |

Executed batch size - 1000 tablets

Brief Manufacturing Procedure:

Step 1: All the raw materials were dispensed as per batch size quantity.

Step 2: The intragranular portion (tafamidis meglumine, lactose monohydrate, microcrystalline cellulose, croscarmellose sodium, and sodium lauryl sulfate) were sifted using #25 mesh and mixed for 10 minutes.

Step 3: Povidone K30 was dissolved in Purified water.

Step 4: Step 2 obtained materials were granulated using povidone binder solution and extra purified water were added until a suitable wet mass were obtained.

Step 5: Wet mass were dried in tray dryer at 60±5° C. until to reach the Loss on drying (LOD) NMT 2.0% w/w.

Step 6: Dried granules were sifted using #25 mesh and retains were milled if required.

Step 7: Croscarmellose sodium (extragranular) was sifted through #25 mesh and blended with step 6 obtained materials for 10 minutes.

Step 8: Step 7 obtained materials were blended with #40 mesh passed colloidal silicon dioxide and Magnesium stearate for 5 minutes.

Step 9: The blend was compressed using suitable tooling with the average tablet weight 140.00 mg.

Table 21 presents dissolution test results for the composition of Example 16 using different dissolution media.

TABLE 21

Dissolution Data for Example 16

Dissolution condition: 900 mL, 75 rpm, USP II (Paddle)

| | Official Media pH 6.8 Phosphate buffer | 0.1N HCl | pH 4.5 Acetate Buffer | Purified Water |
|---|---|---|---|---|
| Example 16 | Tablets not disintegrated/dispersed and found to be intact till 60 min. Tablet found to be slightly swelled due to gelation (rigid gel) with the contact of media. | | | |

Based the Table 21 data of tablets in different dissolution media, it was observed that tablets containing tafamidis meglumine forms gel when contacts with water or other dissolution media.

Example 17. Tafamidis Meglumine Tablets ((Organic Acidifier)

To prevent the gel formation of tablets containing tafamidis meglumine 20 mg, it was decided to acidify the blend using acidifier which may help to disperse the tablets in aqueous buffer media. The prototype composition is presented in below Table 22.

TABLE 22

Prototype composition

| Ingredient | Example 17A | Example 17B |
|---|---|---|
| | mg/tablet | |
| Intra-granular portion | | |
| Tafamidis meglumine | 20.00 | 20.00 |
| Lactose monohydrate 200 mesh | 61.70 | 104.00 |
| Microcrystalline Cellulose (Vivapur PH 101) | 40.00 | — |
| Croscarmellose sodium (Vivasol) | 2.80 | 7.00 |
| Sodium lauryl sulfate (Stepanol WA-100) | 1.40 | 1.40 |
| Povidone (Kollidon K30) | 3.50 | 3.50 |
| Granulating fluid | | |
| Purified water | qs | qs |
| Citric acid anhydrous | 5.00 | 2.00 |
| Extra-granular portion | | |
| Croscarmellose sodium (Vivasol) | 2.80 | — |
| Colloidal silicon dioxide (Aerosil 200) | 1.40 | 1.40 |
| Magnesium stearate | 1.40 | 1.40 |
| Total Tablet weight | 140.00 | 140.00 |

Executed batch size - 1000 tablets

Brief Manufacturing Procedure:

Step 1: All the raw materials were dispensed as per batch size quantity.

Step 2: Intragranular portion (tafamidis meglumine, lactose monohydrate, microcrystalline cellulose, croscarmellose sodium, sodium lauryl sulfate, povidone) were sifted using #25 mesh and mixed for 10 minutes.

Step 3: Citric acid anhydrous was dissolved in Purified water to provide granulating fluid.

Step 4: Step 2 obtained materials were granulated using citric acid solution and extra purified water were added until a suitable wet mass were obtained.

Step 5: Wet mass were dried in tray dryer at 60±5° C. until to reach the Loss on drying (LOD) NMT 2.0% w/w.

Step 6: Dried granules were sifted using #25 mesh and retains were milled in Fitz mill fitted with 0033 screen if required. Step 7: Croscarmellose sodium (extragranular) was sifted through #25 mesh and blended with step 6 obtained materials for 10minutes.

Step 8: Step 7 obtained materials were blended with #40 mesh passed colloidal silicon dioxide and Magnesium stearate for 5 minutes.

Step 9: The blend was compressed using suitable tooling with the average tablet weight 140.00 mg.

The compressed tablets were subjected to physical observation in different dissolution media. The observations are presented below.

TABLE 23a

Dissolution data (pH 6.8 and 0.1N HCl) for Examples 17A-17B

Dissolution condition: 900 mL, 75 rpm, USP II (Paddle)

| | pH 6.8 Phosphate buffer | | 0.1N HCl | |
|---|---|---|---|---|
| | Gel formation Yes/No | Tablet Disintegration/ Dispersion time | Gel formation Yes/No | Tablet Disintegration/ Dispersion time |
| Example 17B | No gelation observed | Within 7 min | No gelation observed | within 10 min |
| Example 17A | No gelation observed | Within 7 min | No gelation observed | within 10 min |

TABLE 23b

Dissolution data (pH 4.5 and purified water) for Examples 17A-17B

Dissolution condition: 900 mL, 75 rpm, USP II (Paddle)

| | pH 4.5 Acetate buffer | | Purified water | |
|---|---|---|---|---|
| | Gel formation Yes/No | Tablet Disintegration/ Dispersion time | Gel formation Yes/No | Tablet Disintegration/ Dispersion time |
| Example 17B | No gelation observed | Within 6 min | No gelation observed | Within 7 minutes |
| Example 17A | No gelation observed | Within 6 min | No gelation observed | Within 7 minutes |

Selection of Dissolution Condition

Based on approval history (USFDA) of tafamidis meglumine soft gelatin capsules 20 mg, the recommended dissolution condition for drug release media is 50 mM Sodium Phosphate buffer pH 6.8, 900 mL, 75 rpm, USP II (Paddle). Basis on this literature evident, the same dissolution condition was chosen as drug release media for tafamidis meglumine tablets 20 mg, i.e., 50 mM Sodium Phosphate buffer pH 6.8, 900 mL, 75 rpm, USP II (Paddle). All trial batches were evaluated in this media for drug release.

In addition to this above-mentioned release media, dissolution was evaluated in purified water to find the drug release rate. Due to poor solubility/insoluble nature of tafamidis meglumine, dissolution was not performed in media like 0.1 N HCl and pH 4.5 acetate buffer.

TABLE 24

Dissolution data (official media and purified water) for Example 17A

| | Batch no. | | | | | | | |
|---|---|---|---|---|---|---|---|---|
| | 5 | 10 | 15 | 20 | 30 | 45 | 60 | Inf |
| Official Media: 50 mM Sodium Phosphate buffer pH 6.8, 900 mL, 75 rpm, USP II Paddle) | | | | | | | | |
| Example 17A | 49 | 62 | 71 | 77 | 83 | 90 | 93 | 96 |
| Purified water, 900 mL, 75 rpm, USP II (Paddle) | | | | | | | | |
| Example 17A | 15 | 18 | 17 | 20 | 22 | 22 | 22 | 21 |

Based on the Table 24 data, it was observed that in the presence of citric acid anhydrous in tablets prevents the gelation phenomena of tablets containing tafamidis meglumine when tablets contacted water or other dissolution media. A possible reason for disintegration/dispersion of tablets into particles may be due to acidifying the blend helps tablets to disperse in buffer medias. In the dissolution, drug release found to be more than 80% w/w at 30 min time point in pH 6.8 phosphate buffer & Purified water. Hence, it was decided to execute the similar experimental trials using various acidifying excipients.

Examples 18-21. Tafamidis Meglumine Tablets (Organic Acidifiers)

In view of the foregoing results, different organic acidifiers (e.g., tartaric acid, malic acid, lactic acid, and fumaric acid) were evaluated to find the effect of acidifier on dispersion of tablets. The compositional makeup of Exs. 18-19 comprising different acidifiers are presented in table 25.

TABLE 25

Compositions makeup of Examples 18-21

| Ingredient(s) | Example 18 | Example 19 | Example 20 | Example 21 |
|---|---|---|---|---|
| | mg/tablet | | | |
| Intra-granular portion | | | | |
| Tafamidis meglumine | 20.00 | 20.00 | 20.00 | 20.00 |
| Lactose monohydrate 200 mesh | 61.70 | 61.70 | 64.70 | 61.70 |
| Microcrystalline Cellulose (Vivapur PH 101) | 40.00 | 40.00 | 40.00 | 40.00 |
| Croscarmellose sodium (Vivasol) | 2.80 | 2.80 | 2.80 | 2.80 |
| Sodium lauryl sulfate (Stepanol WA-100) | 1.40 | 1.40 | 1.40 | 1.40 |
| Povidone (Kollidon K30) | 3.50 | 3.50 | 3.50 | 3.50 |
| Granulating fluid | | | | |
| Purified water | qs | qs | qs | — |
| Absolute alcohol | — | — | — | qs |
| Tartaric acid | 5.00 | — | — | — |
| Malic acid | — | 5.00 | — | — |
| Lactic acid | — | — | 2.00 | — |
| Fumaric acid | — | — | — | 5.00 |
| Extra-granular portion | | | | |
| Croscarmellose sodium (Vivasol) | 2.80 | 2.80 | 2.80 | 2.80 |
| Colloidal silicon dioxide (Aerosil 200) | 1.40 | 1.40 | 1.40 | 1.40 |
| Magnesium stearate | 1.40 | 1.40 | 1.40 | 1.40 |
| Total Tablet weight | 140.00 | 140.00 | 140.00 | 140.00 |

Executed trial batch size - Each batch 1000 tablets

Brief Manufacturing Procedure:

Step 1: All the raw materials were dispensed as per batch size quantity.
Step 2: Intragranular portion (tafamidis meglumine, lactose monohydrate, microcrystalline cellulose, croscarmellose sodium, sodium lauryl sulfate, povidone) were sifted using #25 mesh and mixed for 10 minutes.
Step 3: The respective batch acidifier was dissolved in purified water or alcohol providing granulating fluid.
Step 4: Step 2 obtained materials were granulated using respective batch acidifier containing solution and extra granulating fluid were added until a suitable wet mass were obtained.
Step 5: Wet mass were dried in tray dryer at 60±5° C. until to reach the Loss on drying (LOD) NMT 2.0% w/w.
Step 6: Dried granules were sifted using #25 mesh and retains were milled if required.
Step 7: Croscarmellose sodium (extragranular) was sifted through #25 mesh and blended with step 6 obtained materials for 10 minutes.
Step 8: Step 7 obtained materials were blended with #40 mesh passed colloidal silicon dioxide and magnesium stearate for 5 minutes.
Step 9: The blend was compressed using suitable tooling with the average tablet weight 140.00 mg.

TABLE 26a

Dissolution data (pH 6.8 and 0.1N HCl) for Examples 18-21

Dissolution condition: 900 mL, 75 rpm, USP II (Paddle)

| | pH 6.8 Phosphate buffer | | 0.1N HCl | |
|---|---|---|---|---|
| | Gel formation Yes/No | Tablet Disintegration/ Dispersion time | Gel formation Yes/No | Tablet Disintegration/ Dispersion time |
| Example 18 | No gelation observed | Within 6 min | No gelation observed | within 3 min |
| Example 19 | No gelation observed | Within 4 min | No gelation observed | within 3 min |
| Example 20 | No gelation observed | Within 4 min | No gelation observed | within 4 min |
| Example 21 | No gelation observed | Within 6 min | No gelation observed | within 3 min |

TABLE 26b

Dissolution data (pH 4.5 and purified water) for Examples 18-21

Dissolution condition: 900 mL, 75 rpm, USP II (Paddle)

| | pH 4.5 Acetate buffer | | Purified water | |
|---|---|---|---|---|
| | Gel formation Yes/No | Tablet Disintegration/ Dispersion time | Gel formation Yes/No | Tablet Disintegration/ Dispersion time |
| Example 18 | No gelation observed | Within 5 min | No gelation observed | within 5 min |
| Example 19 | No gelation observed | Within 2 min | No gelation observed | within 2 min |
| Example 20 | No gelation observed | Within 4 min | No gelation observed | within 4 min |
| Example 21 | No gelation observed | Within 5 min | No gelation observed | within 4 min |

TABLE 26c

Dissolution data (official media) for Examples 18-21

Official Media: 50 mM Sodium Phosphate buffer pH 6.8, 900 mL, 75 rpm, USP II Paddle)

| | Batch no. | | | | | | | |
|---|---|---|---|---|---|---|---|---|
| | 5 | 10 | 15 | 20 | 30 | 45 | 60 | Inf |
| Example 18 | 56 | 64 | 73 | 78 | 85 | 90 | 93 | 97 |
| Example 19 | 53 | 65 | 73 | 76 | 82 | 87 | 89 | 90 |
| Example 20 | 52 | 68 | 76 | 81 | 86 | 91 | 92 | 94 |
| Example 21 | 58 | 72 | 78 | 82 | 85 | 88 | 89 | 90 |

Based results of Tables 26a-26c, it was observed that in the presence of different organic acidifier like tartaric acid, malic acid, lactic acid and fumaric acid in tablets prevents the gelation phenomena of tablet containing tafamidis meglumine upon contact with water or other dissolution media. Hence, it was further conforming and clarifies the presence of an acidifier prevents the gelation phenomena of tablet containing tafamidis meglumine. A possible reason for disintegration/dispersion of tablets into particles may be due to acidifying the blend helps tables to disperse in buffer medias. Drug release found to be more than 80% w/w in 30 min time point in pH 6.8 phosphate buffer (official media).

Examples 22-23. Tafamidis Meglumine Tablets (Inorganic Acidifiers)

Different inorganic acidifiers (e.g., hydrochloric acid and phosphoric acid) In order to break the gel formation of tablets containing Tafamidis meglumine 20 mg, it was decided to use different Inorganic acidifiers in the tablets were executed. The prototype composition is presented in below table 27.

TABLE 27

Compositional makeup of Examples 22-23 (tablet)

| Ingredients | Example 22 | Example 23 |
|---|---|---|
| | mg/tablet | |
| Intra-granular portion | | |
| Tafamidis meglumine | 20.00 | 20.00 |
| Lactose monohydrate 200 mesh | 61.70 | 61.70 |
| Microcrystalline Cellulose (Vivapur PH 101) | 40.00 | 40.00 |
| Croscarmellose sodium (Vivasol) | 2.80 | 2.80 |
| Sodium lauryl sulfate (Stepanol WA-100) | 1.40 | 1.40 |
| Povidone (Kollidon K30) | 3.50 | 3.50 |
| Granulating fluid | | |
| Purified water | qs | qs |
| Hydrochloric acid | 2.50 | — |
| Phosphoric acid | — | 3.40 |
| Extra-granular portion | | |
| Croscarmellose sodium (Vivasol) | 2.80 | 2.80 |
| Colloidal silicon dioxide (Aerosil 200) | 1.40 | 1.40 |
| Magnesium stearate | 1.40 | 1.40 |
| Total Tablet weight | 140.00 | 140.00 |

Executed trial batch size - Each batch 1000 tablets

Brief Manufacturing Procedure:

Step 1: All the raw materials were dispensed as per batch size quantity.
Step 2: Intragranular portion (tafamidis meglumine, lactose monohydrate, microcrystalline cellulose, croscarmellose sodium, sodium lauryl sulfate, and povidone) were sifted using #25 mesh and mixed for 10 minutes.
Step 3: The respective inorganic acidifier was dissolved in Purified water to provide granulating fluid.
Step 4: Step 2 obtained materials were granulated using respective batch acidifier containing solution and extra granulating fluid were added until a suitable wet mass were obtained.
Step 5: Wet mass were dried in tray dryer at 60±5° C. until to reach the Loss on drying (LOD) NMT 2.0% w/w.
Step 6: Dried granules were sifted using #25 mesh and retains were milled if required.
Step 7: Croscarmellose sodium (extragranular) was sifted through #25 mesh and blended with step 6 obtained materials for 10 minutes. Step 8: Step 7 obtained materials were blended with #40 mesh passed colloidal silicon dioxide and Magnesium stearate for 5 minutes.
Step 9: The blend was compressed using suitable tooling with the average tablet weight 140.00 mg.

The compressed tablets were subjected to physical observation in different dissolution media. The observations were presented in Tables 28a-28c.

TABLE 28a

Dissolution Data (pH 6.8 and 0.1N HCl) for Examples 22-23

Dissolution condition: 900 mL, 75 rpm, USP II (Paddle)

| | pH 6.8 Phosphate buffer | | 0.1N HCl | |
|---|---|---|---|---|
| | Gel formation Yes/No | Tablet Disintegration/ Dispersion time | Gel formation Yes/No | Tablet Disintegration/ Dispersion time |
| Example 22 | No gelation observed | Within 7 min | No gelation observed | Within 7 min |
| Example 23 | No gelation observed | Within 12 min | No gelation observed | Within 9 min |

TABLE 28b

Dissolution Data (pH 4.5 and purified water) for Examples 22-23

Dissolution condition: 900 mL, 75 rpm, USP II (Paddle)

| | pH 4.5 Acetate buffer | | Purified water | |
|---|---|---|---|---|
| | Gel formation Yes/No | Tablet Disintegration/ Dispersion time | Gel formation Yes/No | Tablet Disintegration/ Dispersion time |
| Example 22 | No gelation observed | Within 5 min | No gelation observed | within 5 min |
| Example 23 | No gelation observed | Within 7 min | No gelation observed | within 12 min |

TABLE 28c

Dissolution data (official media) for Examples 22-23

Official Media: 50 mM Sodium Phosphate buffer pH 6.8, 900 mL, 75 rpm, USP II (Paddle)

| Batch no. | 5 | 10 | 15 | 20 | 30 | 45 | 60 | Inf |
|---|---|---|---|---|---|---|---|---|
| Example 22 | 42 | 59 | 69 | 76 | 83 | 90 | 94 | 96 |
| Example 23 | 43 | 58 | 68 | 69 | 75 | 80 | 84 | 88 |

Based on results shown in Tables 28a-28c, it was observed that in the presence of different inorganic acidifier (e.g., hydrochloric acid and phosphoric acid) in tablets would overcome the gelation phenomena of tablet containing tafamidis meglumine upon contact with water or other dissolution media. Hence, these results confirm that the presence of any inorganic acidifier would prevent the gelation of tablet containing tafamidis meglumine.

Drug release found to be more than 75% w/w in 30 min time point in pH 6.8 phosphate buffer (official media).

Tafamidis Tablets 61 Mg Prototype Formula Development

Based on outcome of tafamidis meglumine tablets 20 mg, the same strategy was applied for tafamidis tablets 61 mg with increase in tablets weight to study the impact of acidifier in tafamidis tablets 61 mg.

Example 24. Tafamidis Tablet (Organic Acidifier)

In order to prevent the gel formation of tablets containing Tafamidis 61 mg, it was decided to acidify the blend using acidifier i.e. citric acid anhydrous. The prototype composition is presented in below table 18.

TABLE 29

Compositional makeup of Example 23 (tablet)

| Ingredient(s) | Example 24 mg/tablet |
|---|---|
| Intra-granular portion | |
| Tafamidis | 61.00 |
| Microcrystalline Cellulose (Vivapur PH 101) | 46.80 |
| Lactose monohydrate 200 mesh | 67.20 |
| Croscarmellose sodium (Vivasol) | 5.00 |
| Sodium lauryl sulfate (Stepanol WA-100) | 2.00 |
| Povidone (Kollidon K30) | 5.00 |
| Granulating fluid | |
| Purified water | qs |
| Citric acid anhydrous | 5.00 |
| Extra-granular portion | |
| Croscarmellose sodium (Vivasol) | 5.00 |
| Colloidal silicon dioxide (Aerosil 200) | 2.00 |
| Magnesium stearate | 1.00 |
| Total Tablet weight | 200.00 |

Executed batch size - 1000 tablets

Brief Manufacturing Procedure:

Step 1: All the raw materials were dispensed as per batch size quantity.

Step 2: Intragranular portion (tafamidis, microcrystalline cellulose, lactose monohydrate, croscarmellose sodium, sodium lauryl sulfate, povidone) were sifted using #25 mesh and mixed for 10 minutes.

Step 3: Citric acid anhydrous was dissolved in Purified water to provide granulating fluid.

Step 4: Step 2 obtained materials were granulated using Citric acid solution and extra purified water were added until a suitable wet mass were obtained.

Step 5: Wet mass were dried in tray dryer at 60±5° C. until to reach the Loss on drying (LOD) NMT 2.0% w/w.

Step 6: Dried granules were sifted using #25 mesh and retains were milled if required.

Step 7: Croscarmellose sodium (extragranular) was sifted through #25 mesh and blended with step 6 obtained materials for 10 minutes.

Step 8: Step 7 obtained materials were blended with #40 mesh passed colloidal silicon dioxide and Magnesium stearate for 5 minutes.

Step 9: The blend was compressed using suitable tooling with the average tablet weight 200.00 mg.

The compressed tablets were subjected to physical observation in different dissolution media. The observations were presented in below.

TABLE 30a

Dissolution Data (pH 6.8 and 0.1N HCl) for Example 23 (tablets)

Dissolution condition: 900 mL, 75 rpm, USP II (Paddle)

| | pH 6.8 Phosphate buffer | | 0.1N HCl | |
|---|---|---|---|---|
| | Gel formation Yes/No | Tablet Disintegration/ Dispersion time | Gel formation Yes/No | Tablet Disintegration/ Dispersion time |
| Example 23 | No gelation observed | Within 5 min | No gelation observed | within 7 min |

TABLE 30b

Dissolution Data (pH 4.5 and purified water) for Example 23 (tablets)

Dissolution condition: 900 mL, 75 rpm, USP II (Paddle)

| | pH 4.5 Acetate buffer | | Purified water | |
|---|---|---|---|---|
| | Gel formation Yes/No | Tablet Disintegration/ Dispersion time | Gel formation Yes/No | Tablet Disintegration/ Dispersion time |
| Example 23 | No gelation observed | Within 10 min | No gelation observed | within 7 min |

TABLE 30c

Dissolution data (official media) for Example 23 (tablets)

Official Media: 50 mM Sodium Phosphate buffer pH 6.8 + 1% Tween 80, 900 mL, 75 rpm, USP II (Paddle)

| | Batch no. | | | | | | | |
|---|---|---|---|---|---|---|---|---|
| | 5 | 10 | 15 | 20 | 30 | 45 | 60 | Inf |
| Example 23 | 36 | 53 | 63 | 68 | 76 | 84 | 88 | 92 |

Based on Table 31 results of tablets in different media, it was observed that in the presence of citric acid anhydrous in tablets prevents the gelation phenomena of tablets containing tafamidis when contacts with water or other dissolution media. A possible reason for disintegration/dispersion of tablets into particles may be due to acidifying the blend using citric acid anhydrous helps to disperse the tablets easily in buffer medias.

We claim:

1. A tablet composition comprising:
   a) Tafamadis or tafamadis meglumine;
   b) at least one acidifier, wherein the at least one acidifier is present in an amount of from about 0.1% w/w to about 10% w/w based on the total weight of the composition; and
   c) at least one pharmaceutically acceptable excipient;
   wherein the tablet comprises 61 mg of tafamadis or 20 mg of tafamadis meglumine.

2. The tablet composition of claim 1, wherein the at least one acidifier comprises a non-toxic organic acid, a non-toxic inorganic acid, or a combination thereof.

3. The tablet composition of claim 1, wherein the at least one acidifier comprises hydrochloric acid, hydrobromic acid, hydroiodic acid, sulfuric acid, sulfamic acid, phosphoric acid, nitric acid, p-toluenesulfonic acid, salicylic acid, methanesulfonic acid, oxalic acid, succinic acid, citric acid, tartaric acid, malic acid, lactic acid, fumaric acid, or a combination thereof.

4. The tablet composition of claim 1, wherein the at least one pharmaceutically acceptable excipient is selected from the group consisting of at least one surfactant; surfactant, disintegrant, binder, diluent, glidant, and lubricant.

5. The tablet composition of claim 1, wherein the at least one pharmaceutically acceptable excipient comprises a surfactant comprising sodium lauryl sulfate, poloxamer, glyceryl monostearate, glyceryl monolaurate, sorbitan monolaurate, sorbitan monostearate, polyethylene glycols, or a combination thereof.

6. The tablet composition of claim 1, wherein the at least one acidifier is present in an amount of from about 1% w/w to about 5% w/w based on the total weight of the composition.

7. The tablet composition of claim 1, wherein the at least one acidifier is present in an amount of from about 3% w/w to about 6% w/w based on the total weight of the composition.

8. The tablet composition of claim 1, wherein the at least one pharmaceutically acceptable excipient comprises a surfactant in an amount of from about 0.1% w/w to about 10% w/w based on the total weight of the composition.

9. The tablet composition of claim 1, wherein the at least one pharmaceutically acceptable excipient comprises a disintegrant comprising crospovidone, croscarmellose sodium, low hydroxypropyl cellulose, starch, sodium starch glycolate, microcrystalline cellulose, alginic acid, polacrillin potassium, or a combination thereof.

10. The tablet composition of claim 1, wherein the at least one pharmaceutically acceptable excipient comprises a disintegrant in an amount of from about 0.5% w/w to about 10% w/w.

11. The tablet composition of claim 1, wherein the at least one pharmaceutically acceptable excipient comprises a disintegrant in an amount of from about 2.5% w/w to about 7.5% w/w.

12. The tablet composition of claim 1, wherein the at least one pharmaceutically acceptable excipient comprises a binder comprising povidone, starch, gelatin, hydroxypropyl cellulose, hydroxypropyl methylcellulose, methyl cellulose, carboxymethyl cellulose, or a combination thereof.

13. The tablet composition of claim 1, wherein the at least one pharmaceutically acceptable excipient comprises a binder in an amount of from about 3% w/w to about 7% w/w.

14. The tablet composition of claim 1, wherein the at least one pharmaceutically acceptable excipient comprises a diluent comprising lactose, microcrystalline cellulose, starch, dicalcium phosphate, mannitol, xylitol, sorbitol, dextrose, fructose, sucrose, maltodextrin, or a combination thereof.

15. The tablet composition of claim 1, wherein the at least one pharmaceutically acceptable excipient comprises a diluent comprising lactose, microcrystalline cellulose, or a combination thereof.

16. The tablet composition of claim 1, wherein the at least one pharmaceutically acceptable excipient comprises a diluent in an amount of from about 20% w/w to about 80% w/w based on the total weight of the composition.

17. The tablet composition of claim 1, wherein the at least one pharmaceutically acceptable excipient comprises a diluent in an amount of from about 40% w/w to about 70% w/w based on the total weight of the composition.

18. The tablet composition of claim 1, wherein the at least one pharmaceutically acceptable excipient comprises a glidant comprising colloidal silicon dioxide, magnesium trisilicate, talc, or a combination thereof.

19. The tablet composition of claim 1, wherein the at least one pharmaceutically acceptable excipient comprises a glidant in an amount of from about 0.1% w/w to about 2% w/w.

20. The tablet composition of claim 1, wherein the at least one pharmaceutically acceptable excipient comprises a lubricant comprising calcium stearate, glycerin monostearate, glyceryl behenate, glyceryl palmitostearate, hydrogenated castor oil, hydrogenated vegetable oil type I, light mineral oil, magnesium lauryl sulfate, magnesium stearate, medium-chain triglycerides, mineral oil, myristic acid, palmitic acid, poloxamer, polyethylene glycol, sodium stearyl fumarate, stearic acid, talc, zinc stearate, or a combination thereof.

21. The tablet composition of claim 1, wherein the at least one pharmaceutically acceptable excipient comprises a lubricant in an amount of from about 0.1% w/w to about 2% w/w.

22. The tablet composition of claim 1 comprising
at least one acidifier in an amount of from about 0.1% w/w to about 10% w/w based on the total weight of the composition;
at least one pharmaceutically acceptable excipient comprising one or more of a diluent, a disintegrant, a surfactant, a binder, a glidant, and a lubricant.

23. The tablet composition of claim 1 comprising Tafamidis meglumine in an amount of about 20 mg;
at least one acidifier in an amount of from about 0.1% w/w to about 10% w/w based on the total weight of the composition;
at least one pharmaceutically acceptable excipient comprising one or more of a diluent, a disintegrant, a surfactant, a binder, a glidant, and a lubricant.

24. The tablet composition of claim 1 comprising
Tafamidis meglumine in an amount of about 20 mg;
at least one acidifier in an amount of from about 2.5% w/w to about 7.5% w/w based on the total weight of the composition;
at least one pharmaceutically acceptable excipient comprising one or more of a diluent, a disintegrant, a surfactant, a binder, a glidant, and a lubricant.

25. The tablet composition of claim 1 comprising
Tafamidis meglumine in an amount of about 20 mg;
at least one acidifier in an amount of from about 4% w/w to about 7.5% w/w based on the total weight of the composition;
at least one pharmaceutically acceptable excipient comprising one or more of a diluent, a disintegrant, a surfactant, a binder, a glidant, and a lubricant.

26. The tablet composition of claim 1 comprising
Tafamidis in an amount of about 61 mg;
at least one acidifier in an amount of from about 0.1% w/w to about 10% w/w based on the total weight of the composition;
at least one pharmaceutically acceptable excipient comprising one or more of a diluent, a disintegrant, a surfactant, a binder, a glidant, and a lubricant.

27. The tablet composition of claim 1 comprising
Tafamidis in an amount of about 61 mg;
at least one acidifier in an amount of from about 2.5% w/w to about 7.5% w/w based on the total weight of the composition;
at least one pharmaceutically acceptable excipient comprising one or more of a diluent, a disintegrant, a surfactant, a binder, a glidant, and a lubricant.

28. The tablet composition of claim 1 comprising Tafamidis in an amount of about 61 mg;
- at least one acidifier in an amount of from about 4% w/w to about 7.5% w/w based on the total weight of the composition;
- at least one pharmaceutically acceptable excipient comprising one or more of a diluent, a disintegrant, a surfactant, a binder, a glidant, and a lubricant.

29. A method for the treatment of the cardiomyopathy of wild type or hereditary transthyretin-mediated amyloidosis in adults to reduce cardiovascular mortality and cardiovascular-related hospitalization, which comprises administering the tablet composition of claim 1 in a patient in need thereof.

\* \* \* \* \*